United States Patent [19]
Manker

[11] Patent Number: 5,058,563
[45] Date of Patent: Oct. 22, 1991

[54] REUSABLE WARMERS OF THE TYPE EMPLOYING A SUPER-COOLED SOLUTION AND AN ACTIVATOR

[75] Inventor: Charles F. Manker, Chicago, Ill.

[73] Assignee: Prism Technologies, Inc., Chicago, Ill.

[21] Appl. No.: 538,838

[22] Filed: Jun. 15, 1990

[51] Int. Cl.⁵ ............................................. F24J 1/00
[52] U.S. Cl. ..................................... 126/263; 126/204; 128/403
[58] Field of Search .............. 126/263, 204; 62/4, 62/112; 128/402, 403, 399, 401; 422/245; 252/70; 428/596; 165/10

[56]  References Cited
U.S. PATENT DOCUMENTS 4,295,517 10/1981 Guex et al. ........................ 126/263
4,572,158  2/1986 Fiedler ............................... 126/263
4,574,051  3/1986 Matthews et al. ..................... 252/70
4,780,117 10/1988 Lahey ................................ 126/263
4,865,012  9/1989 Kelley ............................... 126/263
4,872,442 10/1989 Manker .............................. 126/263
4,880,953 11/1989 Manker .............................. 126/263

Primary Examiner—James C. Yeung
Attorney, Agent, or Firm—Leydig, Voit & Mayer

[57]  ABSTRACT

The present invention provides reusable warmers of the supersaturated solution type that are substantially free of saddlebagging. The reusable warmers comprise a flexible container, and located within the container, a supercooled salt solution, an activator for initiating crystallization of the supercooled salt solution, and a gelling agent, the gelling agent being present in sufficient quantity to convert the salt solution to a gel.

1 Claim, 1 Drawing Sheet

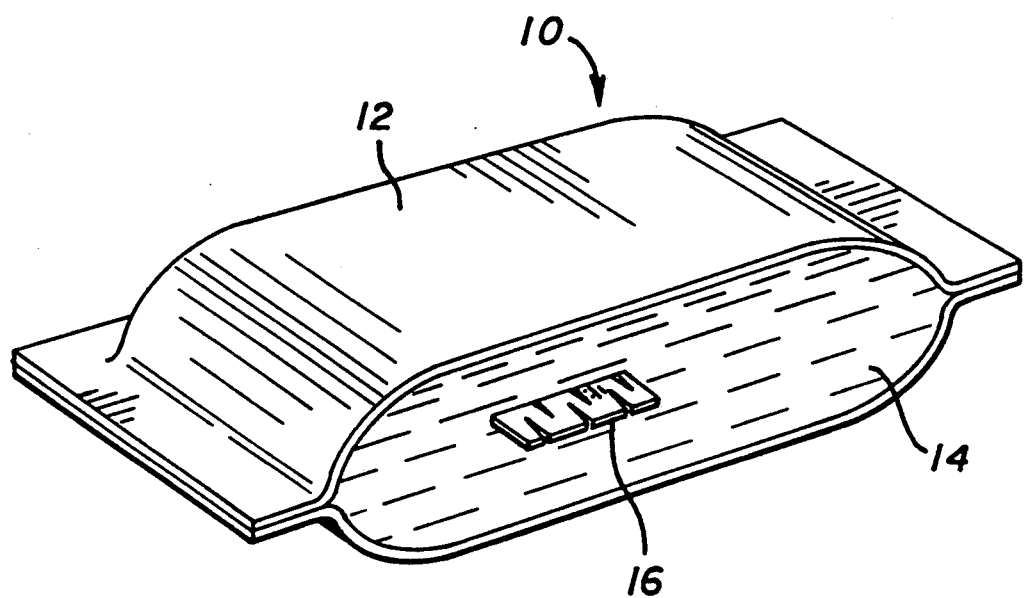

REUSABLE WARMERS OF THE TYPE EMPLOYING A SUPER-COOLED SOLUTION AND AN ACTIVATOR

FIELD OF THE INVENTION

This invention relates to reusable warmers for directly applying heat to areas of the human body to relieve muscle aches, pains and the like which employ a super-cooled aqueous solution (as for example, a super-cooled, super-saturated aqueous sodium acetate solution) and an activator to initiate the crystallization of the super-cooled liquid. Under certain conditions the unit may also be used to apply cold to the body.

BACKGROUND OF THE INVENTION

Reusable warmers employing a super-cooled aqueous solution and an activator have been used by sportsmen and others for years to warm parts of the human body. Such a reusable warmer is shown, for example, in U.S. Pat. No. 4,077,390 to Stanley et al. (issued Mar. 7, 1978) generally at FIG. 1 and described generally at column 1, line 59 to column 2 line 4 as being a sealed bag-like flexible receptacle (such as polyethylene, nylon and the like) containing a super-cooled aqueous sodium acetate and an activator comprising a flexible metal strip having one or more slits or fissures. Another type of activator is described in my U.S. Pat. No. 4,872,442 (issued Oct. 10, 1989). That activator is characterized by a plurality of slits in a flexible metal article, with the opposing sides of the slits being in contact along at least a part of the length of the slit, and by an eroded and roughened surface on said article which comprises a number of minute metal nodules attached to and protruding from the surface, especially at or near the slit, which nodules are adapted to be detached or broken-off upon flexing of the activator.

The super-cooled sodium acetate solution contained in the bag-like receptacle is activated by flexing or bending the activator strip. Upon activation, the sodium acetate in the super-cooled solution crystallizes and heat (i.e. the "heat of crystallization") is evolved. Reuse of the warmer is accomplished by merely reheating the container contents to dissolve the crystallized sodium acetate and once again form the super-cooled sodium acetate solution. This can be done by either immersing the warmer in boiling water or by heating the warmer in a microwave oven for a time sufficient to dissolve the crystallized sodium acetate.

One of the primary uses for such reusable warmers is the application of heat directly to various parts of the human body to relieve muscle aches and pains. Other uses include those by sports participants (such as hunters, skiers and the like) or sports enthusiasts (such as spectators at sporting events) who use the warmers to keep various parts of their bodies warm during cold weather. However, the human body in general is contoured and not flat. Moreover, the person using the reusable warmer may be standing, sitting or walking. For these reasons the reusable warmer is for the most part not applied in a horizontal position (i.e. not flat).

It has been found that during use the super-cooled aqueous solution in the reusable warmer being a liquid will flow in the plastic bag (as, for example, around a leg or arm) and form areas in the bag having too much solution leaving other areas with too little. This phenomenon has been referred to as "saddle bagging."

Saddle bagging leads to uneven coverage by the reusable warmer of the body part area to be heated. Heretofore, the art has attempted to minimize saddle bagging by various means. These have included, for example, adding welds to the flexible, sealed container of the warmer so that the solution is restrained from freely flowing. Also the use of very heavy gauge plastics which will not only be more resistant to bending, but will also act to restrain flow of the super-cooled solution and keep a more flat surface have been tried. None of these means has proved satisfactory, since they render the reusable warmer less comfortable and more difficult to use. It has been found that users of the reusable warmers prefer relatively flexible containers made of relatively thin materials such as polyethylene and nylon (i.e., low cost, non vinyl packages) and when such materials are used the problem of super-cooled solution migration and the resulting saddle bagging is accentuated and cannot be readily solved by conventional means, as, for example, by weld placement. Adding welds also results in a less flexible and more expensive product.

SUMMARY OF THE INVENTION

I have found that the problem of saddle bagging in a reusable warmer of the type which comprises a sealed bag-like flexible receptacle (such as polyethylene, nylon and the like) containing a super-cooled aqueous sodium acetate and an activator comprising a flexible metal article, preferably having one or more slits or fissures, may be overcome by incorporating a small amount of a viscosity increasing agent such as, for example, CELLOSIZE ® HEC-QP 52000-H gelling agent (Union Carbide Corporation). The viscosity increasing agent makes the super-cooled sodium acetate solution viscous enough to delay, prevent or inhibit the natural tendency of the solution to flow around body parts which are not flat, yet allows the reusable warmer to be flexible enough so that it readily conforms to the contours of the body part to which it is being applied, making the reusable warmer more comfortable and easier to use.

BRIEF DESCRIPTION OF THE DRAWING

The drawing illustrates a reusable warmer of the present invention comprising a flexible bag-like container, a super-cooled salt solution and an activator.

DESCRIPTION OF THE PREFERRED EMBODIMENT

The present invention makes an improvement in reusable warmers containing super-cooled sodium acetate solution and an activator (sometimes called a "trigger"). That improvement comprises incorporating a small amount of a viscosity increasing agent (sometimes referred to as "gelling" or "thickening agents") in the super-cooled sodium acetate solution during the manufacture of the reusable warmer; which amount is sufficient to substantially inhibit the flow of the salt solution, particularly after it has been activated and is in the warm state. The exact type of viscosity increasing, gelling or thickening agent is not critical to the present invention and any number of commercially available viscosity increasing agents may be employed without departing from the spirit and scope of the invention.

One example of such suitable materials are Union Carbide Corporation's CELLOSIZE ® Hydroxyethyl Cellulose (HEC) gelling agents which are non-ionic, water-soluble polymers. Other water-soluble natural polymers (such as the gums, starches, celluloses, gelatin, etc.) and other chemically modified derivates of the same which are commonly used as thickeners, suspending agents, gelling agents, emulsifiers or dispersants may also be employed, provided that the material causes the solution to gel or increase in viscosity sufficiently to inhibit or slow-down the flow of the solution during the heat producing phase.

The method of making a reusable warmer is well known and does not form an essential part of my herein-described invention. Any of several methods of manufacture can be employed as, for example, that which is described in the aforementioned U.S. Pat. No. 4,077,390 at columns 2 and 3. Further, the type of activator used also is not an essential part of my invention and any suitable activator or trigger can be used. As, for example, the activators described in the aforementioned U.S. Pat. Nos. 4,077,390 or 4,872,422.

The essential element is the incorporation of a small amount of a viscosity increasing agent (such as, for example, Union Carbide's CELLOSIZE® gelling agent) into the super-cooled sodium acetate solution during manufacture of the reusable warmer. The amount of viscosity increasing, thickening or gelling agent used can vary depending upon the specific type of reusable warmer being made. However, the amount used should not be so small that the viscosity of the super-cooled sodium acetate solution is so low that the solution flows to an appreciable extent and collects in low spots in the bag (and cause saddle bagging), nor should it be so great that the viscosity of the super-cooled solution is so high that the reusable warmer is not flexible and, therefore, not comfortable to use. I have found that when hydroxyethyl cellulose is used as the viscosity increasing agent, the amount of gelling agent used can be less than about 5% by weight of the super-cooled solution and, preferrably, between about 1 to 4% by weight.

In the FIGURE, there is illustrated a reusable warmer 10, in accordance with the present invention. The warmer comprises a flexible bag-like container 12 which has contained therein a super-cooled salt solution 14 into which there has been incorporated a viscosity increasing agent. Also housed within the container 12 is an activator 16 for initiating the crystallization of the super-cooled salt solution.

The invention can further be best described by the following examples.

EXAMPLE 1

Into an empty vinyl bag sealed along three sides, there was introduced a 50% sodium acetate solution at 200 degrees Fahrenheit containing a ratio of 3 by weight CELLOSIZE® HEC-QP 52000-H (Union Carbide Corporation), in an amount sufficient to fill the bag, and an activator of the type generally described in U.S. Pat. No. 4,872,442. The bag was then totally sealed and allowed to cool at ambient temperature over a period of about two (2) hours. The cooling time could be reduced by immersion of the warmer in cold water or by placing it in a refrigerator. After the two hours a viscous super-cooled sodium acetate solution formed which was gelatinous in nature. The gelatinous super-cooled solution was generally clear and transparent and the activator inside the reusable warmer readily could be seen.

When the reusable warmer was activated (by flexing the activator) it provided the same level of warmth for the same period of time as did similar reusable warmers which did not contain any Cellosize ® HEC-QP 52000-H. The thickened or gelatinous super-cooled sodium acetate solution was stable (it did not separate into its component parts) and did not attack the container. The concentration of the super-cooled salt solution can be varied depending on the temperature to be achieved by activation. It was found that the gelatinous super-cooled solution cushioned and suspended the activator so that the danger of accidental activation during manufacture, shipping or storing of the reusable warmer was substantially reduced.

EXAMPLE 2

A reusable warmer was assembled similar to the one in Example 1, except 2 to 3% by weight of CELLOSIZE® HEC-QP 100000-H (Union Carbide Corporation) was employed instead of the CELLOSIZE® HEC-QP 52000-H used in Example 1. As in Example 1, a viscous super-cooled sodium acetate solution formed which was gelatinous in nature. The gelatinous super-cooled solution was generally clear and transparent and the activator inside the reusable warmer readily could be seen.

When the reusable warmer was activated (by flexing the activator) it provided the same level of warmth for the same period of time as did similar the reusable warmer of Example 1. The thickened or gelatinous super-cooled sodium acetate solution was stable (it did not separate into its component parts) and did not attack the container.

EXAMPLE 3

A reusable warmer was assembled similar to the one in Example 1, except that between 10-30% by weight of a corn starch was used as the viscosity increasing agent. During assembly of the reusable warmer, considerable care must be taken in mixing in the starch because it tended to form lumps easily. Mixing was performed using high shear mixers. The assembled reusable warmer, after heating, was not as clear as the reusable warmers of Examples 1 and 2. However, its stability was good.

The reusable warmer of the present invention can be used as a "cold pack" by placing it in a refrigerator for a short period. It is apparent that the salt (sodium acetate) contained in the cold pack sufficiently reduces the freezing temperature of the water so that freezing does not take place. When used in this fashion the cold pack has many of the same advantages that it has when used as a reusable warmer; it holds temperature well and conforms to the area of the body to which it is applied. The stability of the cold pack when used in this fashion is highly dependent on the purity of the water and the acetate used in its manufacture; the greater the purity of the solution, the lower the temperature that the cold pack can be used at. For temperatures down to 25 degrees Farenheit tap water and standard acetate is acceptable.

It will be apparent to those skilled in this art that various changes may be made in the construction and form of the reusable warmer employing a gelatinous super-cooled solution and in the details of the method of manufacture without departing from the spirit and scope of this invention, and that the specific directions and forms shown herein are presented for the purpose of making an understandable disclosure of the invention and are not intended to be any restriction on the scope thereof, other than as defined in the accompanying claims.

I claim:

1. In a reusable warmer employing a flexible bag-like container, a super-cooled salt solution and an activator for initiating the crystallization of said super-cooled salt solution, the improvement comprising incorporating into said super-cooled salt solution an effective amount less than about 5% by weight of a viscosity increasing agent sufficient to form a gel and substantially inhibit the flow of said super-cooled salt solution, wherein the viscosity increasing agent is a non-ionic, water-soluble hydroxyethyl cellulose polymer.

* * * * *